United States Patent [19]

Louis et al.

[11] Patent Number: 4,600,731

[45] Date of Patent: Jul. 15, 1986

[54] PASTE COMPOSITION CONTAINING AN ORGANOPOLYSILOXANE, PLATINUM AND FILLER

[75] Inventors: Eckhart Louis; Wolfgang Hechtl; Heinz Hefner, all of Burghausen, Fed. Rep. of Germany

[73] Assignee: Wacker-Chemie GmbH, Munich, Fed. Rep. of Germany

[21] Appl. No.: 705,163

[22] Filed: Feb. 25, 1985

[30] Foreign Application Priority Data

Mar. 13, 1984 [DE] Fed. Rep. of Germany ....... 3409139

[51] Int. Cl.⁴ .............................................. A61K 6/10
[52] U.S. Cl. .................... 523/109; 433/214; 524/474; 524/493; 524/861; 524/862
[58] Field of Search ............... 523/109; 524/861, 862, 524/474, 493; 433/214; 106/35

[56] References Cited

U.S. PATENT DOCUMENTS

| | | | |
|---|---|---|---|
| 3,950,300 | 4/1976 | Hittmair et al. | 523/109 |
| 4,035,453 | 7/1977 | Hittmair et al. | 523/109 |
| 4,096,159 | 6/1978 | Hechtl et al. | 556/434 |
| 4,273,902 | 6/1981 | Tomioka et al. | 525/475 |
| 4,468,484 | 8/1984 | Pellico | 523/109 |

*Primary Examiner*—Lorenzo B. Hayes

[57] ABSTRACT

A paste composition which is used in the preparation of dental impression compositions containing:

(a) at least 100 ppm by weight, based on the weight of the paste composition of platinum calculated as the element;

(b) 35 to 75 percent by weight, based on the weight of the paste composition, of a diorganopolysiloxane which contains at least 2 SiC-bonded vinyl groups per molecule and has a viscosity of at least 100 mPa.s at 25° C.;

(c) 10 to 25 percent by weight, based on the weight of the paste composition, of a hydrocarbon which is liquid or spreadable at room temperature and is free of aliphatic carbon-carbon multiple bonds; and (d) 3 to 15 percent by weight, based on the weight of the paste composition, of hydrophobic silicon dioxide having a surface area of at least 50 $m^2/g$;

in which the sum of the percentages of (a) to (d) including other additives which may be present in the paste composition is equal to 100 percent. The paste composition is mixed with the other ingredients of the dental impression compositions such as diorganopolysiloxanes having SiC-bonded vinyl groups, organopolysiloxanes having at least 3 Si-bond hydrogen atoms per molecule and filler to form dental impression compositions.

6 Claims, No Drawings

PASTE COMPOSITION CONTAINING AN ORGANOPOLYSILOXANE, PLATINUM AND FILLER

The present invention relates to dental impression compositions and more particularly to paste compositions which are used in dental impression compositions.

BACKGROUND OF THE INVENTION

Pastes which are used in preparing dental impression compositions containing platinum, organopolysiloxanes and fillers are known. These dental impression compositions contain triorganosiloxy terminated diorganopolysiloxanes having SiC-bonded vinyl groups in the terminal units, an organopolysiloxane which contains at least 3 Si-bonded hydrogen atoms per molecule, a platinum catalyst for the addition of the Si-bonded hydrogen to the vinyl groups and a filler as the essential ingredients. These pastes have been added to the other components of the compositions in a weight ratio which range from 1:1 to 7:1. U.S. Pat. No. 4,273,902, to Tomioka et al, discloses in Example 1 forming a paste by mixing a dimethylpolysiloxane having vinyldimethylsiloxy terminal groups with quartz, calcium carbonate and a platinum-siloxane complex and then adding 7 parts of the paste to 1 part of hydrogenmethylpolysiloxane. In Example 2 of the patent, a paste composition containing a hydroxyl-terminated vinylmethylpolysiloxane, quartz, zirconium silicate and chloroplatinic acid is added in a 1:1 ratio to a composition containing a hydroxyl-terminated vinylmethylpolysiloxane, hydrogenmethylpolysiloxane and finely divided quartz.

One advantage of using a paste composition such as described in the present invention is that the amount of platinum catalyst required is substantially reduced while attaining more uniformity in the crosslinking behavior of the composition after storing the paste for a period of time. Also, the use of a small amount of paste in the dental impression compositions avoids testing large quantities of the paste containing platinum, organopolysiloxane and filler. Another advantage of using the paste composition of this invention in dental impression compositions is that the paste composition containing platinum, organopolysiloxane and filler can be rapidly and easily kneaded with the other components of the composition with the bare hands without leaving any trace of the composition on the hands. Still another advantage of the present invention is that the components of the dental impression composition consisting of a diorganopolysiloxane having SiC-bonded vinyl groups, an organohydrogenpolysiloxane containing at least 3 Si-bonded hydrogen atoms per molecule and filler can be stored together.

Therefore, it is an object of the present invention to provide a paste composition which may be combined with the other components of dental impression materials. Another object of the present invention is to provide a paste composition containing a diorganopolysiloxane having SiC-bonded vinyl groups, a platinum catalyst, a hydrocarbon and a hydrophobic filler. Still another object of the present invention is to provide a dental impression composition in which only a small amount of platinum catalyst is required and still achieve uniform cross-linking of the dental impression composition. A further object of the present invention is to provide a dental impression composition in which the diorganopolysiloxane having SiC-bonded vinyl groups, an organohydrogenpolysiloxane having at least 3 Si-bonded hydrogen atoms per molecule and filler can be stored together.

SUMMARY OF THE INVENTION

The foregoing objects and others which will become apparent from the following description are accomplished in accordance with this invention, generally speaking, by providing a paste composition which may be combined with a dental impression composition containing triorganosiloxy terminated diorganopolysiloxanes having SiC-bonded vinyl groups in each terminal unit, an organopolysiloxane having at least 3 Si-bonded hydrogen atoms per molecule and a filler, in which the paste composition comprises (a) at least 100 ppm by weight of platinum, calculated as the element and based on the weight of the platinum-containing paste composition;

(b) 35 to 75 percent by weight, based on the weight of the platinum-containing paste composition, of a diorganopolysiloxane which contains at least 2 SiC-bonded vinyl groups per molecule and has a viscosity of at least 100 mPa.s at 25° C.;

(c) 10 to 25 percent by weight, based on the weight of the platinum-containing paste composition of a hydrocarbon, which is liquid or spreadable at room temperature and is free of aliphatic carbon-carbon multiple bonds; and (d) 3 to 15 percent by weight, based on the weight of the platinum-containing paste composition, of a hydrophobic silicon dioxide having a surface area of at least 50 m$^2$/g, in which the sum of the percentages of the components (a) to (d), including other additives which may be present in the composition is equal to 100 percent by weight. The platinum-containing paste composition is preferably combined with the other components of a dental impression composition consisting of a diorganopolysiloxane having SiC-bonded vinyl groups, an organopolysiloxane having at least 3 Si-bonded hydrogen atoms per molecule and filler in an amount up to about 10 percent by weight based on the weight of the components of the dental impression composition other than the platinum-containing paste composition.

DETAILED DESCRIPTION OF THE INVENTION

These paste compositions which are combined with the other components of a dental impression composition contain (a) a platinum compound or complex;

(b) a diorganopolysiloxane having at least 2 SiC-bonded vinyl groups per molecule;

(c) a hydrocarbon which is liquid or spreadable at room temperature and is free of aliphatic unsaturated carbon-carbon bonds;

(d) a hydrophobic silicon dioxide having a surface area of at least 50 m$^2$/g and other additives, if desired, such as pigments, fragrances and agents which control the rate of the platinum catalyzed addition of the Si-bonded hydrogen to SiC-bonded vinyl groups.

The platinum (a) can be present in any form in which it promotes the addition of Si-bonded hydrogen to SiC-bonded vinyl groups in a reasonably short period of time in the mouth of a patient, such as required of dental impression compositions. Generally, compounds or complexes of platinum are used, such as platinum-vinylsiloxane complexes and particularly platinum-1,3-divinyl-1,1,3,3-tetramethyldisiloxane complexes, with or without a detectable amount of inorganic halogen, or complexes produced from $H_2Pt.Cl_6.6H_2O$ and an alkanol.

The pastes of this invention preferably contain from 500 to 1500 ppm (parts by weight per million parts by weight) platinum, calculated as the element and based on the total weight of the platinum-containing paste to be mixed with the other components of the dental impression composition.

The diorganopolysiloxanes (b) which contain at least 2 SiC-bonded vinyl groups per molecule preferably have the formula

wherein R is the same or different and represents SiC-bonded organic radicals free of aliphatic carbon-carbon multiple bonds; R' is a vinyl group or is the same as R and n is a whole number with a value such that the viscosity of the diorganopolysiloxane is from 100 to 300,000 mPa.s at 25° C. and more preferably from 1000 to 100,000 mPa.s The preferred organic radicals represented by R are hydrocarbon radicals which contain from 1 to 18 carbon atoms per radical. Preferred examples of such radicals are alkyl radicals such as the methyl, ethyl, n-propyl and isopropyl radicals as well as the octadecyl radicals; cycloalkyl radicals such as the cyclohexyl radical and methylcyclohexyl radicals; aryl radicals such as the phenyl radical; alkaryl radicals such as the tolyl radicals and aralkyl radicals such as the benzyl radical and the B-phenylethyl radical. The hydrocarbon radicals represented by R may also be substituted with halogenated hydrocarbon radicals or cyanoalkyl radicals which are inert with respect to the other components of the dental impression compositions. Examples of substituted radicals are hydrocarbon radicals such as the 3,3,3-trifluoropropyl radical, o-, p- and m- chlorophenyl radicals and cyanoalkyl radicals such as the B-cyanoethyl radical. It is preferred that at least 80 percent of the number of radicals be methyl radicals.

The hydrocarbon substance which is liquid or spreadable at room temperature and is free of aliphatic multiple bonds preferably has a boiling point of at least 250° C. at 1000 mbar (abs.). Paraffin oil or petroleum or the use of both paraffin oil and petroleum are preferred.

The values for the silicon dioxide surface area are the BET values, that is, values determined by nitrogen adsorption in accordance with ASTM Special Technical Publication No. 51, 1941, page 95.

Pyrogenically produced silicon dioxide is the preferred silicon dioxide from which the hydrophobic silicon dioxide (d) is produced; however, it may also be produced by precipitation. The silicon dioxide may be reacted with organohalosilanes such as dimethyldichlorosilane, organoalkoxysilanes such as trimethylethoxysilane or hexaorganodisilazanes such as hexamethyldisilazane to impart hydrophobic properties thereto. When the silicon dioxide is treated with a hexaorganodisilazane, the silicon dioxide can be treated in the presence of the diorganopolysiloxane (b). It is preferred that the silicon dioxide be hydrophobicized with a gaseous organosilicon compound.

In addition to components (a) to (d), the pastes of this invention may also contain other additives. For example, the pastes may contain pigments, soluble dyes, fragrances and agents which control the rate of the platinum catalyzed addition of Si-bonded hydrogen to SiC-bonded vinyl groups. Examples of agents which control the rate of addition are diorgano(poly)siloxanes which contain at least 2 SiC-bonded vinyl groups and have a viscosity of at most 50 mm²/s at 25° C., such as 1,3-divinyl-1,1,3,3-tetramethyldisiloxane.

The pastes of this invention are preferably mixed in an amount of from 0.5 to 10 percent by weight and more preferably from 1 to 5 percent by weight based on the weight of the components of the dental impression composition comprising a diorganopolysiloxane having triorganosiloxy-terminal groups in which each terminal unit contains a SiC-bonded vinyl group, an organopolysiloxane which contains at least 3 Si-bonded hydrogen atoms per molecule and filler as the essential components.

The components of the dental impression composition comprising a diorganopolysiloxane having triorganosiloxy-terminal groups, in which each terminal unit contains a SiC-bonded vinyl group, an organopolysiloxane which contains at least 3 Si-bonded hydrogen atoms per molecule and filler can be the same diorganopolysiloxane, organopolysiloxane having at least 3 Si-bonded hydrogen atoms per molecule and fillers used heretofore and be present in the same quantities as in the dental impression compositions described, for example, in U.S. Pat. No. 3,950,300 to Hittmair et al; German patent application (Offenlegungsschrift) No.25 08 56 to Dow Corning Ltd; European patent application No.00 46 907 to Bayer AG; U.S. Pat. No. 4,273,902 to Tomioka et al; or U.S. Pat. No. 4,096,159 to Hechtl. The dental impression compositions are well known and have been described in the art.

It is preferred that the dental impression composition have a dough-like consistency before crosslinking, that is, that it contain from 1.5 to 2.5 parts of filler per part of total organopolysiloxane and that prior to the addition of the platinum-containing paste of this invention, the organopolysiloxane which contains at least 3 Si-bonded hydrogen atoms in each molecule be mixed with the triorganosiloxy-terminated diorganopolysiloxane, in which each terminal unit contains a SiC-bonded vinyl group and the other components of the dental impression composition, except for the paste composition of this invention and stored as a single mixture.

The dental impression composition having a dough-like consistency consisting of a triorganosiloxy-terminated diorganopolysiloxane, in which each terminal unit contains a SiC-bonded vinyl group, an organopolysiloxane which contains at least 3 Si-bonded hydrogen atoms per molecule, filler and the paste of this invention are particularly suitable as dental impression compositions.

All parts and percentages or ppm in the following examples are by weight unless otherwise specified.

The platinum catalyst mixture consisting of a platinumvinylsiloxane complex and diluent used in the following examples and comparison examples was prepared in the following manner.

About 20 parts of sodium bicarbonate were added to a mixture containing 10 parts of $H_2PtCl_6.6H_2O$, 20 parts of 1,3-divinyl-1,1,3,3-tetramethyldisiloxane and 50 parts of ethanol. The mixture was heated at reflux for 30 minutes with stirring, then allowed to stand for 15 hours and then filtered. The volatile components were distilled from the filtrate at approximately 16 hPa (abs.). About 17 parts of a liquid were obtained as residue. This was dissolved in benzene, then filtered and the benzene was distilled from the filtrate. The residue was mixed with a dimethylpolysiloxane diluent having dimethylvinylsiloxane terminal units and a viscosity of 1400 mPa.s at 25° C. in such an amount that the mixture contains 1 weight percent platinum, calculated as the element.

EXAMPLE 1

(a) About 360 parts of anhydrous dimethylpolysiloxane having dimethylvinylsiloxy terminal groups and a viscosity of 18,000 mPa.s at 25° C. are mixed in a planetary mixer at room temperature and under ambient pressure, that is, at approximately 1000 hPa (abs.), with 105 parts of paraffin oil, 30 parts of commercial white pigment powder made into a paste with a trimethylsiloxy terminated dimethylpolysiloxane which is liquid at room temperature, 42 parts of commercial silicon dioxide which has been treated with dimethyldichlorosilane to impart hydrophobic properties thereto, and having a surface area of $120\pm30$ $m^2/g$ (see Chemiker-Zeitung, 1965, pages 437 to 440) and 43 parts of a mixture prepared by mixing (A) 35 parts of the platinum-vinylsiloxane complex prepared above, containing 1 percent platinum calculated as the element;

(B) 4 parts of a trimethylsiloxy terminated diorganopolysiloxane consisting of 66.66 mol percent of dimethylsiloxane units and 33.33 mol percent of methylvinylsiloxane units and a viscosity of 10 $mm^2/s$; and (C) 4 parts of a dimethylvinylsiloxy terminated dimethylpolysiloxane having a viscosity of 18,000 mPa.s at 25° C. A soft, creamy, white paste is obtained which contains organopolysiloxane, filler and 600 ppm of platinum calculated as the element and based on the total weight of the paste. It is stored at room temperature or at 70° C. for 7 days before use.

(b-1). About 834 parts of the anhydrous dimethylvinylsiloxy terminated dimethylpolysiloxane having a viscosity of 18,000 mPa.s at 25° C. and 760 parts of anhydrous diatomaceous earth are mixed in a planetary mixer at room temperature and 100 hPa (abs.). About 1370 parts of anhydrous cristobalite meal are added in increments and mixed into the mixture. The mixture thus obtained is stirred in the planetary mixer for another hour at 100 hPa (abs.) after the addition of the cristobalite is completed and for an additional 0.5 hours at 100 hPa (abs.) after 172 parts of paraffin oil has been added. Subsequently, the mixture is then stored at room temperature for 14 days.

(b-2). About 2700 parts of the mixture prepared in accordance with the procedure described in paragraph (b-1) above are kneaded at room temperature under ambient pressure with 15 parts of chrome oxide green and 75 parts of an anhydrous dimethylhydrogensiloxane terminated diorganopolysiloxane consisting of dimethylsiloxane units and methylhydrogensiloxane units (10 dimethylsiloxane units per methylhydrogensiloxane unit) and having a viscosity of 150 mPa.s at 25° C. The trapped air is removed by kneading at 100 hPa (abs.). The mixture is then stored for 7 days at room temperature or at 70° C. under anhydrous conditions.

(b-3). A portion of the mixture prepared in accordance with the procedure described in paragraph (b-2) above, is mixed with 2 percent based on the weight of mixture, of the paste prepared in (a) above so that the finished composition contains 12 ppm of platinum. Only 35 seconds are required to mix 32 g of the mixture whose preparation is described above containing 0.64 g of the platinum-containing paste to form a uniform color from the green and white pigments. The composition thus obtained is allowed to crosslink at room temperature.

EXAMPLE 2

The procedure described in Example 1(b-3) is repeated except that 1 percent paste prepared in accordance with Example 1(a) is substituted for 2 percent of the paste so that the finished composition contains 6 ppm of platinum.

EXAMPLE 3

The procedure described in Example 1(b-3) is repeated except that 0.5 percent of paste produced in accordance with Example 1(a) is substituted for 2 percent of the paste so that the finished composition contains 3 ppm of platinum.

Comparison Example $V_1$ (a) About 290 parts of the mixture whose preparation is described in Example 1(b-1) are kneaded under 100 hPa (abs.) with 2.763 parts of a mixture which was prepared by mixing components (A), (B) and (C) in accordance with the procedure of Example 1, 60 parts of anhydrous diatomaceous earth and 15 parts of commercial white pigment powder made into a paste with a trimethylsiloxy terminated dimethylpolysiloxane which is liquid at room temperature. The mixture thus obtained contains 75 ppm platinum and is stored for 7 days at room temperature or at 70° C. under anhydrous conditions.

(b) One part of the mixture whose preparation is described in Comparison Example $V_1$(a) above is mixed with 1 part of the mixture whose preparation is described in Example 1(b-2) above, to form a finished composition which contains 37.5 ppm of platinum. About 50 seconds were required to mix 16 g of the mixture whose preparation was described in (a) above with 16 g of the other mixture. The composition thus obtained is allowed to crosslink at room temperature.

Comparison Example $V_2$

The procedure described in Comparison Example $V_1$(a) is repeated except that 1.843 parts of the mixture of components (A), (B) and (C) are used in Comparision Example $V_1$(a) above, instead of 2.763 parts so that the finished composition contains 25 ppm platinum.

Comparision Example $V_3$

The procedure described in Comparison Example $V_1$(a) is repeated, except that 0.871 parts of the mixture of components (A), (B) and (C) are used in Comparison Example $V_1$(a), above, instead of 2.763 parts so that the finished composition contains 12.5 ppm platinum.

The following table shows that by using the pastes of this invention, the quantity of available platinum can be reduced and only a slight change in the crosslinking behavior of the composition occurs when the paste is stored prior to mixing with the other components of the composition.

TABLE

| Examples or Comparison Examples | Pt ppm | Storage at | Pot life** Seconds | Shore A hardness after x minutes x = | | | | | | | | | | |
|---|---|---|---|---|---|---|---|---|---|---|---|---|---|---|
| | | | | 6** | 7 | 8 | 9 | 10 | 11 | 12 | 20 | 30 | 60 | 90 |
| 1 | 12 | RT*** | 140 | 60 | 68 | 70 | 70 | 70 | | | | | | |
| 1 | 12 | 70° C. | 140 | 60 | 67 | 68 | 68 | 68 | | | | | | |
| 2 | 6 | RT | 135 | 49 | 62 | 65 | 67 | 69 | | | | | | |
| 2 | 6 | 70° C. | 140 | 60 | 68 | 69 | 69 | 69 | | | | | | |
| 3 | 3 | RT | 155 | 43 | 52 | 61 | 68 | 70 | | | | | | |
| 3 | 3 | 70° C. | 150 | 51 | 62 | 69 | 71 | 71 | | | | | | |
| $V_1$ | 37.5 | RT | 165 | 42 | 58 | 68 | 73 | 74 | 74 | 74 | | | | |
| $V_1$ | 37.5 | 70° C. | 160 | 45 | 67 | 63 | 68 | 70 | 71 | 71 | | | | |
| $V_2$ | 25 | RT | 155 | 60 | 71 | 73 | 73 | 73 | | | | | | |
| $V_2$ | 25 | 70° C. | 245 | | | 5 | 13 | 27 | | 39 | 61 | 66 | | |
| $V_3$ | 12.5 | RT | 180 | | 36 | 47 | 55 | 59 | | 65 | 70 | | | |
| $V_3$ | 12.5 | 70° C. | 930 | | | | | | | | | | 37 | 47 |

*time between the beginning of mixing in stage (b-3) of the examples or in stage (b) of the Comparison Examples and crosslinking.
**in minutes after the beginning of mixing in stage (b-3) of the examples or stage (b) of the Comparison Examples.
***RT = room temperature.

What is claimed is:

1. A paste composition containing platinum, an organopolysiloxane an filler which is combined with a triorganosiloxy terminated diorganopolysiloxane having SiC-bonded vinyl groups in each terminal unit, an organopolysiloxane containing at least 3 Si-bonded hydrogen atoms per molecule, and filler to form a dental impression composition, in which the past composition contains
   (a) at least 100 ppm by weight of platinum, calculated as the element and based on the weight of the paste composition;
   (b) 35 to 75 percent by weight, based on the weight of the paste composition, of a diorganopolysiloxane containing at least 2 SiC-bonded vinyl groups in each molecule and having a viscosity of at least 100 mPa.s at 25° C.;
   (c) 10 to 25 percent by weight, based on the weight of the paste composition, of a hydrocarbon which is liquid or spreadable at room temperature and is free of aliphatic carbon-carbon multiple bonds; and
   (d) 3 to 15 percent by weight based on the weight of the paste composition, of hydrophobic silicon dioxide having a surface area of at least 50 $m^2/g$;
in which the sum of the percentages in the paste composition including paste additives is equal to 100 percent.

2. The paste composition of claim 1, wherein from 500 to 1500 ppm by weight of platinum, calculated as the element and based on the toal weight of the paste composition, is present in the paste composition.

3. The paste composition of claim 1, wherein the hydrocarbon (c) has a boiling point of at least 250° C. at 1000 mbar (abs.).

4. The paste composition of claim 1, wherein the hydrocarbon (c) is a paraffin oil.

5. The paste composition of claim 1, wherein the hydrocarbon (c) is petroleum having a boiling point of at least 250° C. at 1000 mbar (abs.).

6. A dental impression composition containing a triorganosiloxy terminated diorganopolysiloxane having SiC-bonded vinyl groups in each terminal unit, an organopolysiloxane containing at least 3 Si-bonded hydrogen atoms per molecule, a filler and a paste composition in an amount of from 0.5 to 10 percent by weight based on the weight of the triorganosiloxy terminated diorganopolysiloxane having SiC-bonded vinyl groups in each terminal unit, the organopolysiloxane having at least 3 Si-bonded hydrogen atoms per molecule and filler, said paste composition containing
   (a) at least 100 ppm by weight of platinum, calculated as the element and based on the weight of the paste composition; (b) 35 to 75 percent by weight, based on the weight of the paste composition, of a diorganopolysiloxane containing at least 2 SiC-bonded vinyl groups in each molecule and having a viscosity of at least 100 mPa.s at 25° C.;
   (c) 10 to 25 percent by weight, based on the weight of the paste composition, of a hydrocarbon which is liquid or spreadable at room temperature and is free of aliphatic carbon-carbon multiple bonds; and
   (d) 3 to 15 percent by weight based on the weight of the paste composition of hydrophobic silicon dioxide having a surface area of at least 50 $m^2/g$; in which the sum of the percentages in the paste composition including paste additives is equal to 100 percent.

* * * * *